(12) United States Patent
Balashov et al.

(10) Patent No.: US 10,312,162 B2
(45) Date of Patent: Jun. 4, 2019

(54) METHODS AND APPARATUS FOR SEMICONDUCTOR SAMPLE WORKFLOW

(71) Applicant: FEI Company, Hillsboro, OR (US)

(72) Inventors: Konstantin Balashov, Beaverton, OR (US); Tom Miller, Portland, OR (US)

(73) Assignee: FEI COMPANY, Hillsboro, OR (US)

( * ) Notice: Subject to any disclaimer, the term of this patent is extended or adjusted under 35 U.S.C. 154(b) by 0 days.

(21) Appl. No.: 15/615,494

(22) Filed: Jun. 6, 2017

(65) Prior Publication Data
US 2017/0363549 A1 Dec. 21, 2017

Related U.S. Application Data

(60) Provisional application No. 62/352,730, filed on Jun. 21, 2016.

(51) Int. Cl.
H01L 21/66 (2006.01)
G01N 9/24 (2006.01)
G01N 1/28 (2006.01)
G03F 7/20 (2006.01)
G01N 23/20025 (2018.01)
G01N 23/2204 (2018.01)

(52) U.S. Cl.
CPC ............ H01L 22/12 (2013.01); G01N 1/28 (2013.01); G01N 9/24 (2013.01); G01N 23/20025 (2013.01); G01N 23/2204 (2013.01); G03F 7/70483 (2013.01)

(58) Field of Classification Search
CPC ...... G01N 1/28; G01N 1/2806; G01N 1/2813; G01N 1/286; G01N 1/2873; H01J 37/20; H01L 22/12
USPC ... 250/440.11, 442.11, 492.1, 492.2, 492.21, 250/492.3
See application file for complete search history.

(56) References Cited

U.S. PATENT DOCUMENTS

| 2013/0291925 | A1* | 11/2013 | Okuuchi | H01L 31/02363 136/246 |
| 2014/0084157 | A1* | 3/2014 | Miller | H01J 37/3023 250/307 |
| 2016/0233191 | A1* | 8/2016 | Zhang | H01L 24/92 |
| 2016/0247661 | A1* | 8/2016 | Plachinda | H01J 37/222 |

* cited by examiner

Primary Examiner — Jason L McCormack
(74) Attorney, Agent, or Firm — Denton W. McAlister

(57) ABSTRACT

Apparatus and methods are described for the automated transfer and storage of transmission electron microscope (TEM) and scanning/transmission electron microscope (STEM) lamella samples throughout a semiconductor manufacturing facility using existing automation infrastructure such as a Front Opening Unified Pod (FOUP). Also provided are wafer facsimiles corresponding to outer dimensions of semiconductor, data storage or solar cell wafers, wherein the facsimiles adapted to store, carry and/or provide a testing platform for testing of samples taken from semiconductor, data storage or solar cell wafers.

14 Claims, 7 Drawing Sheets

METHODS AND APPARATUS FOR SEMICONDUCTOR SAMPLE WORKFLOW

CROSS REFERENCE TO RELATED APPLICATIONS

This application claims priority based on based on U.S. Provisional Application Ser. No. 62/352,730 filed Jun. 21, 2016, which is incorporated herein by reference in its entirety.

FIELD OF THE INVENTION

This invention relates generally to methods and apparatus for evaluation of samples of semiconductor chips and data storage wafers, including for analysis by Transmission Electron Microscopy (TEM) and/or Scanning Transmission Electron Microscopy (STEM) as well as TEM related techniques including Energy Dispersive Spectroscopy (EDS) and Electron Energy Loss Spectroscopy (EELS).

BACKGROUND OF THE INVENTION

Without limiting the scope of the invention, its background is described in connection with existing sampling of semiconductor wafers and data storage wafers. Data storage substrates (wafers) are similar in overall appearance to semiconductor wafers but are typically composed of different materials.

A semiconductor substrate on which circuits are formed is usually a thin disk of a crystalline semiconductor material, most typically silicon, and is termed a wafer. A wafer is formed by slicing a grown crystal ingot or boule. After lapping the wafer into a uniform thickness and surface homogeneity, the wafers are polished to a mirror finish and cleaned. The prepared wafers are then ready for integrated circuit fabrication. In a semiconductor fabrication plant or "FAB," the wafers are transferred through repeated sequential steps of thermal oxidation, photolithography, etching, doping, and repetitions of the same prior to deposition of metal and dielectric layers and further etching. This process of formation of semiconductor circuits requires sophisticated automated movement of wafers through a clean room environment in the FAB as the microelectronics are formed on the wafer surface. A typical modern FAB will include hundreds of pieces of specialized equipment. The amount of processing that the semiconductor wafer undergoes increases with the complexity of the circuit design. Thus, a 300 mm wafer may travel from 8 to 10 miles during processing, while visiting over 200 process tools to undergo hundreds of individual processing steps.

Wafers are transferred through the FAB in a multi-wafer carrier that is referred to as a FOUP, which stands for Front Opening Unified (or Universal) Pod. Similarly, FOUPS are used to transport and store data storage wafers. Both semiconductor wafers and data storage wafers are round planar disks and FOUPs are available that are generally designed to hold the various dimensions of available wafers and disks.

Present state-of-the-art semiconductor manufacturing is performed using 300 mm wafers although the industry is transitioning to 450 mm wafers and larger diameter wafers are contemplated as larger cylindrical crystalline boules are grown.

Ultimately, the circuits on the finished semiconductor wafers are inspected for fundamental elemental characteristics and on-wafer function and performance. As part of this inspection process, the critical dimensions of the wafer are measured, typically by high resolution imaging at sub-nanometer resolution levels. The industry standard method of obtaining the best resolution of the submicroscopic structure of a region of a semiconductor circuit is by scanning electron microscopy (SEM) and/or transmission electron microscopy (TEM). With an SEM, a primary electron beam is focused to a fine spot that scans the surface of the wafer to be observed. Secondary electrons are then emitted from the surface as it is impacted by the primary beam, and these secondary electrons are detected by the SEM to form an image. Using a TEM, a broad beam of electrons is directed at the sample surface, and electrons that are transmitted through the sample are focused to form an image. With TEM imaging, the sample must be sufficiently thin to allow the electrons in the broad beam to travel through the sample and exit on the opposite side. An imaging technique similar to TEM is STEM imaging. In STEM imaging, thin samples are also required but a focused probe is formed at the sample plane. The acronyms (S)TEM or STEM are used to indicate imaging with either STEM or TEM. In addition, other capabilities may be present in certain electron microscopes including Energy Dispersive Spectroscopy (EDS), Energy Dispersive X-ray Spectroscopy (EDX) and Electron Energy-Loss Spectroscopy (EELS). For purposes of these evaluations, (S)TEM samples are cut from the wafers and imaged by (S)TEM as well as other analyses for which the samples are suitable.

Several techniques are known for preparing TEM samples for imaging, including cleaving, chemical polishing, mechanical polishing, broad beam low energy ion milling, or a combination thereof. The disadvantage to these methods is that they are not site-specific and often require that the starting material be sectioned into smaller and smaller pieces, thereby destroying much of the original sample. Other techniques generally referred to as "lift-out" techniques use focused ion beams ("FIB") to cut the sample from a substrate or bulk sample without destroying or damaging surrounding parts of the substrate. Such techniques are useful in analyzing the results of processes used in the fabrication of the resulting integrated circuits. Techniques where the sample is extracted from the substrate within the FIB system vacuum chamber are commonly referred to as "in-situ" techniques while sample removal outside of the vacuum chamber (as when the entire wafer is transferred to another tool for sample removal) are called "ex-situ" techniques.

A TEM sample is a sample that has been thinned to a sufficient level so as to be electron transparent in a region of interest (ROI) for TEM analysis. The ROI is typically about 2×2 μm in size. The actual TEM sample removed from a semiconductor wafer is typically called a "lamella," and may have overall dimensions of about 15×8 μm and a thickness of about 15 nm in the ROI. One of the preferred technologies for making a TEM sample at a customer-specified location is to use the focused ion beam (FIB) method set forth above. Typically, a microscope combining both an FIB and an SEM are utilized for creating site-specific TEM lamellae. Such combined FIB-SEM tools are often called "dual beam" lamella production tools.

The resulting lamella samples may then be positioned on a TEM grid that is compatible for use with TEM, SEM or STEM equipment for imaging. There are a large variety of formats of TEM grids, but they are generally designed to be compatible with TEM, SEM or STEM sample holders. Effectively, the sample holders are designed to hold a 3 mm circle or some fraction thereof. As such, there is an industry standard format for TEM grids, which are typically about 3 mm in diameter and about 500 μm thick at the rim. One company that manufactures such grids is Ted Pella, Inc. of Redding, Calif. Generally, there are two types of TEM grids, one where lamella are placed onto the grid and held in place purely by naturally occurring electrostatic forces, and another where lamella are affixed to a region on the grid through an attachment process. Once the lamellae are placed or affixed to the TEM grid, they are then typically manually positioned in the TEM apparatus for imaging.

Whatever methods are used, the preparation of a TEM sample is complex and time consuming. Many of the steps involved in the TEM sample preparation and analysis must be performed using instruments operated manually, which decreases efficiency and increases manufacturing costs. Indeed, some steps require manual movement of the lamellae from one piece of equipment to the next. For example, prepared lamellae samples are typically removed from the TEM sample preparation tool and stored in grid storage boxes, dishes or vials from which individual grids are manually loaded into the TEM imaging tool. The loss of automation at certain stages is a significant detriment to semiconductor chip manufacture. From the foregoing, it appeared to the present inventors that the lamella sample storage and transport system could be greatly improved. Provided herein are innovative workflow control and storage systems and apparatus for preparing, transporting, and imaging samples taken from semiconductor chips.

BRIEF SUMMARY OF THE INVENTION

Provided herein are improved methods and apparatus by which semiconductor samples may be stored and moved between different pieces of equipment used in the semiconductor manufacturing process using FOUPs. In one embodiment a wafer or disk facsimile is provided for use in storing and transporting testing samples taken from a semiconductor or data storage wafer. In certain embodiments, the wafer facsimile includes a body dimensioned to correspond generally to dimensions of a semiconductor wafer or data storage wafer being tested, and a plurality of niches formed in a surface of the body and configured to receive one or more test samples. In certain embodiments, the plurality of niches of the wafer or disk facsimile are configured to directly receive a test sample while in other embodiments the plurality of niches are EM grid receptacles configured to receive EM grids. The niches may include grid retainers such as, for example, lids or clips. The test samples may include electron microscope (EM) lamella such as transmission electron microscope (TEM) and/or scanning/transmission electron microscope (STEM) lamella.

In certain embodiments, the wafer or disk facsimile includes a body formed of a rigid material configured to be received in a front opening unified pod (FOUP). Suitable rigid materials include but are not limited to ceramic, plastic, metal and/or silicon materials.

In certain embodiments, the wafer or disk facsimile further includes at least one sub-carrier positioned on or in the exposed surface of the wafer facsimile, wherein the at least one sub-carrier is configured to carry a plurality of EM grids such that the sub-carrier may be loaded directly into a vacuum chamber of the EM.

The plurality of niches on the wafer or disk facsimile may be indexed such that each test sample received therein is identifiable to a semiconductor wafer from which the test sample was taken. In certain embodiments, the plurality of niches are indexed using a barcode or an RFID tag. Also provided are methods for storing and transporting electron microscope (EM) lamella, including the steps of loading one or more lamella into a front opening unified pod (FOUP), transporting the FOUP to an EM using an automated material handling system, unloading the one or more lamella from the FOUP, and loading the lamella into the EM. In certain embodiments, the one or more lamella are attached to a wafer facsimile and the wafer facsimile is loaded into the FOUP. In other embodiments, the EM grids are disposed in a sample tower mounted in the FOUP.

In other embodiments, a receptacle for TEM lamella referred to as a "solar cell facsimile" is provided that can be moved by automated material handling systems in the solar cell industry. Thus, in certain embodiments, TEM samples are placed in the "solar-cell facsimile" and moved in a manufacturing environment by an existing material handling systems for storage and analysis.

BRIEF DESCRIPTION OF THE DRAWINGS

For a more complete understanding of the present invention, including features and advantages, reference is now made to the detailed description of the invention along with the accompanying figures.

DETAILED DESCRIPTION OF THE INVENTION

Figure 1A:
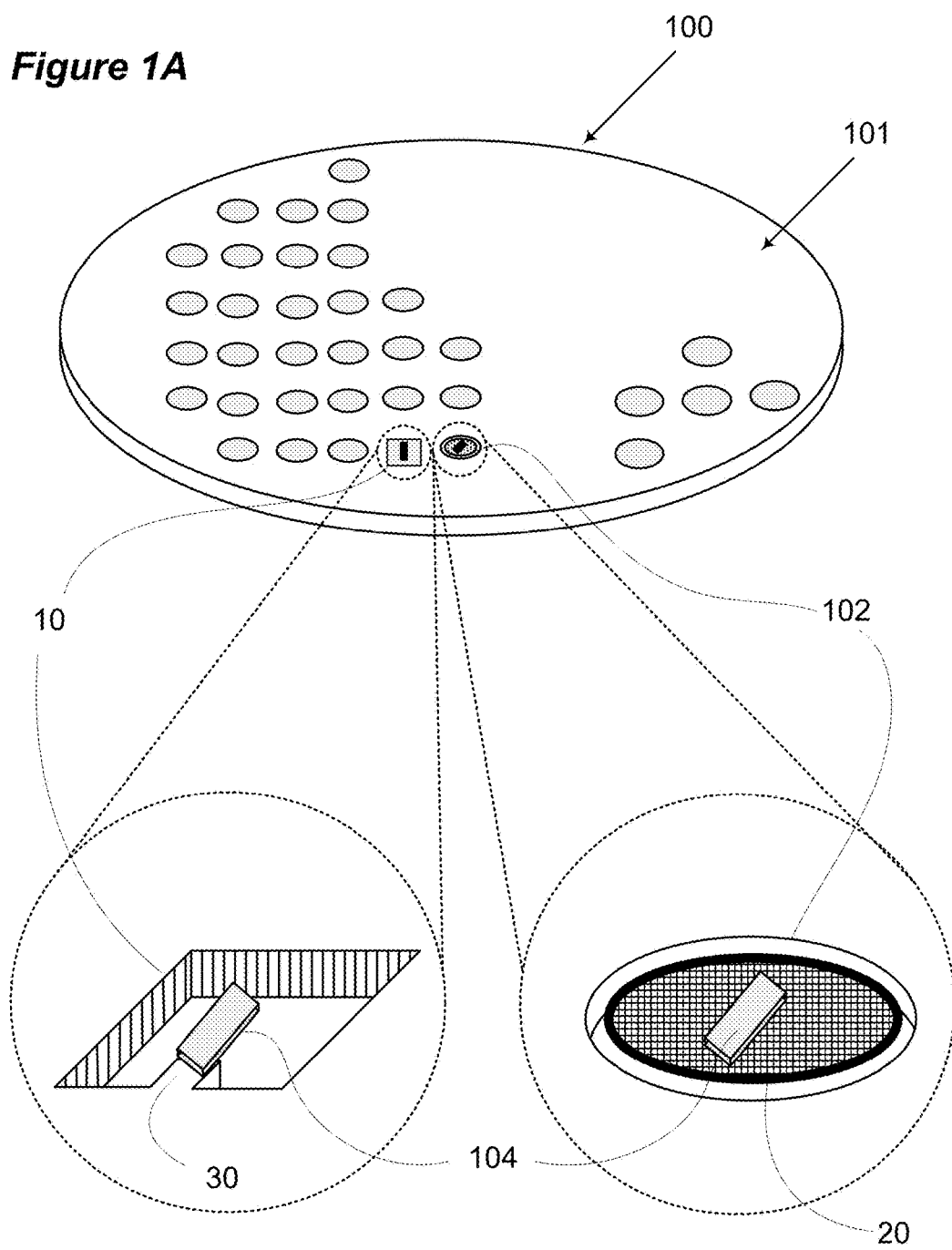
FIG. 1A illustrates a top perspective view of a wafer facsimile including two types of sample niches according to certain embodiments of the present invention.

The invention is primarily directed to the automated transfer and storage of test samples in a semiconductor manufacturing environment, such as a FAB, or a data storage environment, wherein the transfer and storage is able to better and more fully utilize existing automated technology. The apparatus and methods are particularly suited to transfer and storage of TEM lamella samples but may be employed for any type of testing that involves samples removed from a wafer for testing. As used herein, the term "EM lamella samples" may be interpreted to include TEM, SEM and STEM lamella samples as well as other analytical techniques such as, for example, Dual Beam, EDS, EDX, and EELS techniques that require similar sample preparation and/or storage and transport processes. The methods and apparatus disclosed herein are also suitable for use in the data storage industry, particularly for the manufacture and analysis of hard-drive samples.

While the making and using of various embodiments of the present invention are discussed in detail below, it should be appreciated that the present invention provides many applicable inventive concepts which can be employed in a wide variety of specific contexts. The specific embodiment discussed herein are merely illustrative of specific ways to make and use the invention and do not delimit the scope of the invention.

Abbreviations

The following abbreviations are used throughout this application:
AMHS Automated Material Handling System
Dual Beam FIB/SEM system
EBSD Electron BackScatter Diffraction
EDS Energy Dispersive Spectroscopy
EDX Energy Dispersive X-Ray Spectroscopy
EELS Electron Energy-Loss Spectroscopy
EM Electron Microscope or microscopy
FAB Semiconductor Fabrication plant
FIB Focused Ion Beam
FOUP Front Opening Unified Pod
ROI Region of Interest
SEM Scanning Electron Microscopy
STEM Scanning/Transmission Electron Microscopy
TEM Transmission Electron Microscope or microscopy
WIP Work In Progress
WFT Wafer Final Test To facilitate the understanding of this invention, and for the avoidance of doubt in construing the claims herein, a number of terms are defined below. Terms defined herein have meanings as commonly understood by a person of ordinary skill in the areas relevant to the present invention. The terminology used to describe specific embodiments of the invention does not delimit the invention, except as outlined in the claims.

The use of terms such as "a," "an," and "the" are not confined to refer to a singular entity unless explicitly so defined, but include the general class of which a specific example may be used for illustration. The use of the terms "a" or "an" may therefore mean any number that is at least one, including "one," "one or more," "at least one," and "one or more than one."

The term "or" means any of the alternatives and any combination of the alternatives, including all of the alternatives, unless the alternatives are explicitly indicated as mutually exclusive.

Similarly, for the avoidance of doubt and unless otherwise explicitly indicated to refer to alternatives as mutually exclusive, the phrase "at least one of" when combined with a list of items, means a single item from the list or any combination of items in the list. The phrase does not require all of the listed items unless explicitly so defined.

The terms "comprising" (and any form thereof such as "comprise" and "comprises"), "having" (and any form thereof such as "have" and "has"), "including" (and any form thereof such as "includes" and "include") or "containing" (and any form thereof such as "contains" and "contain") are inclusive or open-ended and do not exclude additional, unrecited elements or method steps.

As previously described, the preparation of TEM lamella samples is a complex process. In one embodiment, TEM lamella may be prepared by "lift-out" techniques that use focused ion beams ("FIB") to cut the sample from a substrate or bulk sample. A Dual Beam tool may be utilized to form lamella samples using in-situ or ex-situ lift out methods. With in-situ lift-out, for example, a lamella may be cut from the bulk sample and then FIB-welded to a TEM grid inside the tool that performed the lamella preparation. With ex-situ lift-out, for example, the lamella may reside in the actual wafer to be tested. Once the lamella is formed in the wafer, the wafer is removed from the lamella preparation tool and a separate piece of equipment is used to lift out the lamella from the wafer and deposit it onto a conventional TEM grid. An example of an ex-situ method is disclosed in U.S. Pat. No. 8,357,913 and is incorporated herein by reference.

Using either method, there are two generalized types of TEM grid sample attachments that may be utilized: (1) lamellae samples are placed onto the grid and are held in place purely by naturally occurring electrostatic forces; or (2) lamellae samples are affixed to a region on the grid through an attachment process such as by FIB-welding. For the latter process, an example of such a commercially available grid is the "PELCO® FIB Lift-Out TEM Grid" manufactured by Ted Pella, Inc. The methods of the invention apply to both types of grids. As used herein, the term "EM grid" is used to refer to grids for use in Electron Microscopes whether they be TEM, SEM or STEM as well as grids used for Dual Beam, EDS, EDBS, EDX, and EELS techniques etc. Most commonly the tool used to image the lamella would be generically called a TEM even if it had STEM and other analytical analysis capabilities.

Once the lamella are positioned on the EM grid (using either method), the EM grid may then be transferred, typically manually, to a grid storage container that is manually moved in the FAB. Grids are then also manually removed from the grid storage container to the EM imaging tool for analysis.

The invention is directed to automating the workflow process of transferring lamella to an EM grid and transferring the EM grid to the EM imaging apparatus for imaging. In one embodiment disclosed herein, an improved method is provided by which lamella are moved in an automated manner between different pieces of equipment in the semiconductor environment. In one aspect, the methods provide an improved and more efficient method of storing and transporting the lamella from a piece of equipment in the FAB that creates or manipulates the lamella ("Tool A"), to the tool that images the lamella ("Tool B"). For example, Tool A may be a lamella production tool, or alternatively, a tool that "plucks" a lamella from the sample (e.g., a wafer), such as the tool used to perform ex-situ lift-out methods as described above. Tool B may be an electron microscope (EM), such as a transmission electron microscope (TEM), scanning electron microscope (SEM) or a scanning/transmission electron microscope (STEM).

In one embodiment, the lamella are moved, stored and indexed using an existing automation infrastructure present in modern semiconductor factories (FABs). This automation infrastructure is sometimes called an Automated Material Handling System (AMHS). An example of a suitable AMHS is disclosed in U.S. Pat. No. 8,197,172 and is incorporated herein by reference. In modern semiconductor FABs, semiconductor wafers are moved around the FAB in FOUPs (Front Opening Unified Pod). FOUPs are typically designed to transport a batch of twenty-five 300 mm (diameter)

wafers around the FAB and to isolate the wafers from the clean room environment. Regardless of the dimension of the wafer, FOUPs respective to the required wafer dimensions are utilized. Movement of semiconductor wafers using FOUPs in conjunction with an AMHS is also described in U.S. Pat. No. 8,197,172 referenced above.

Another industry in which similar robotics and FOUPs to those used in a FAB is the data storage industry where disks or wafers are transported and stored in FOUPs much like the semiconductor wafers described in detail here. In one embodiment, test samples of the data storage wafers are transported and stored in FOUPs much like the semiconductors wafers described in detail here including on Sample Carry On Wafers or "SCOWs."

In one embodiment provided herein using the disclosed facsimile wafers, FOUPs are used to move not only the wafers being tested, but also testing samples such as TEM lamella, thereby allowing for improved and automated connectivity between the testing tool (Tool B) and upstream sample production tools (Tool A). The FOUPs not only provide for lamella storage and transport, but they also deliver the lamella samples directly to the TEM imaging tool for analysis.

In a preferred embodiment, each piece of equipment used in the AMHS, including for example the lamella preparation tool and TEM or STEM imaging tool, is operably connected to (or integrated with) a computer which uses software to implement sample creation and processing and is further adapted to index and follow the sample through storage and testing. Any suitable software applications, modules, and components (conventional and/or self-generated) may be used for implementing the software. For example, an automated STEM sample management system may be implemented using IC3D™ software for automated machine control and metrology, which is commercially available from FEI Company of Hillsboro, Oreg. In this way, movement of semiconductor material around the FAB using the AMHS is automated so that it may be more efficient.

According to one embodiment of the invention, EM lamella samples are moved around the FAB using conventional FOUPs. However, standard FOUPs are currently designed and configured to receive semiconductor wafers, not EM lamella, which are significantly smaller. In certain embodiments apparatus are provided that allow for storage and transport of the lamella using FOUPs, without the need to modify or re-design the FOUPs and/or AMHS already in use although modified FOUPs are also contemplated that are designed to specifically accommodate test samples while being adapted to be transferred by the same AMHS that carries wafers through the FAB.

TEM samples are also utilized for analysis and quality control of solar cells and are used to understand manufacturing issues associated with the solar cell industry. Solar cells as typically produced today are manufactured on crystalline silicon wafers. The solar cells may be cut from boules as they are for semiconductor wafers or if multi-crystalline, may be cut from ingots. Work-flows discussed earlier in relation to the semiconductor industry or data storage industry also have applicability to the solar cell industry. In the case of the solar cell industry, automated material handling systems may not use FOUP pods to transport material, but may instead move material in another form factor. The solar cell form factor may be adapted to contain TEM lamella. A receptacle for TEM lamella that can be moved by automated material handling systems in the solar cell industry will be referred to as a "solar cell facsimile." In certain embodiments, TEM samples are placed in the "solar-cell facsimile" and moved in a manufacturing environment by an existing material handling system to the TEM.

The following examples are included for the sake of completeness of disclosure and to illustrate the methods of the present invention. In no way are these examples intended to limit the scope or teaching of this disclosure. As set forth in each of the examples below, a FOUP is ultimately used to carry wafer testing samples such as EM lamella from the lamella preparation tool to the EM analysis tool.

Example 1

In one embodiment, existing factory automation, such as FOUPs in conjunction with an AMHS, are used to move EM lamellas around a FAB. In order to implement this embodiment, wafer facsimiles 100 such as are depicted in FIG. 1A are provided that are dimensioned to correspond generally to the size of the wafers being subject to testing such that they will fit in a respective FOUP and can be transported using AMHS. A non-limiting term coined here for such a wafer facsimile is a "Sample Carry On Wafer" or "SCOW." The wafer facsimile (SCOW) may be formed of a disk-shaped body having at least one surface 101 on which test samples are deposited and stored. While not limited to any particular design, the wafer facsimiles (SCOWs) preferably have the same size and shape as the semiconductor wafers or date storage wafers from which the test samples are taken. In one example, the wafer facsimiles (SCOWs) may have a diameter of about 300 mm and a thickness of about 0.775 mm. In another embodiment, the wafer facsimiles (SCOWs) may have a diameter of about 450 mm and a thickness of about 0.925 mm. In yet another embodiment, the thickness of the wafer facsimile (SCOW) may be slightly thicker than the semiconductor or data storage wafer from which the test samples are taken and still be compatible with wafer and FOUP handling equipment. The wafer facsimile (SCOW) may be formed of a ceramic material, glass, metal, silicon, plastic, carbon fiber or any other materials known to one skilled in the art to be suitable for sample storage and transport in a FOUP.

On certain embodiments as depicted in FIG. 1A, one surface 101 of the wafer facsimile 100, will include a plurality of sample niches, each of which is dimensioned to hold a test sample 104 either directly such as niche 10 or mounted on a sample support such niche 102, which is depicted showing a test sample 104 such as for example an EM lamella on an EM grid 20. As depicted in FIG. 1, the sample niches may be generally square or rectangular such as niches 10 or may be generally round or oval such as niches 102. As depicted in FIG. 1A, the sample niches such as niche 10 may be provided with an attachment platform 30 to which samples are directly attached. The platforms can be of various configurations including the depicted projection from a side of the niche or, as sample niche 10 is depicted in FIG. 1B, the sample platform may be configured as a generally central sample post 40 on which the sample may be directly placed.

Figure 1B:
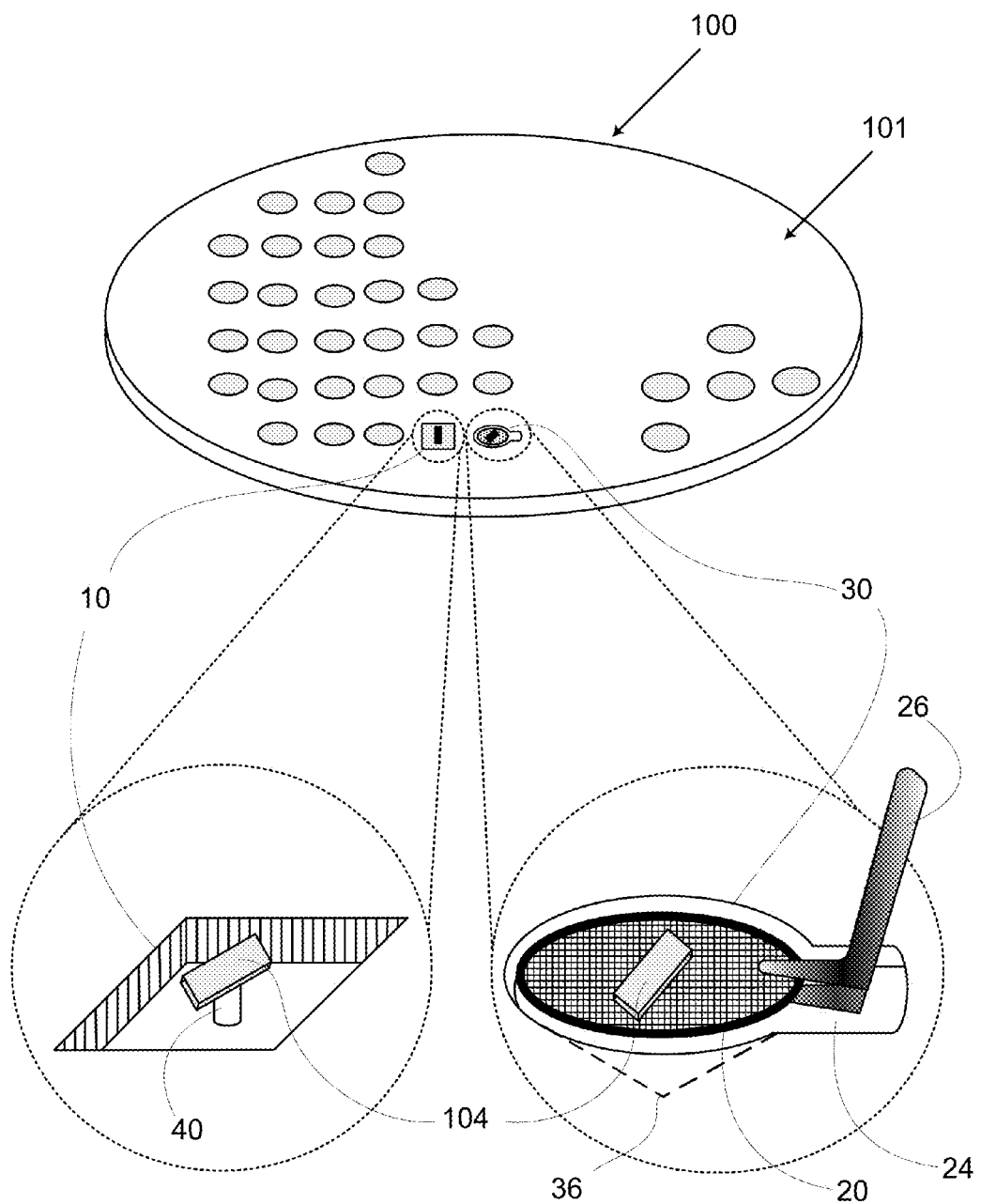
FIG. 1B illustrates a top perspective view of a wafer facsimile including two different types of sample niches according to other embodiments.

On alternative embodiments such as depicted in FIG. 1B, one surface 101 of the wafer facsimile 100, will include a plurality of sample niches each of which is dimensioned to hold a test sample 104 either directly such as niche 10 or mounted on a sample support such niche 30, which is depicted showing a test sample 104 such as for example an EM lamella on an EM grid 20. As depicted in FIG. 1B, the sample niches such as the depicted niche 30 may be provided with an access depression 34 to allow grasping equipment such as micromanipulator 26 to pick up either the sample directly or the sample mounted on a sample support such as the depicted EM grid. Access depressions may be available on sample niches regardless of their configuration as generally square, rectangular, round or oval. Where designed for holding EM grids the sample niche may include a post on which the EM grid rests (not shown) or may include a central underlying channel (not shown) that allows micromanipulators to conveniently grasp the sample from below and above it. Other configurations are envisioned including where the floor of the sample niche is conical such as the depicted dashed line 36. The combined conical depression with access depression allows grasping equipment to readily capture a corner of the EM grid.

As set forth above, a standard TEM lamella typically has dimensions of about 15×8 μm and a thickness of about 15 nm. As such, while not limited to any particular design, the sample niches preferably are sized so as to be able to receive the sample to be tested. Thus, where the sample is an EM lamella, the EM lamella niches are dimensioned to hold an EM grid. In one embodiment, the wafer facsimile has a plurality of niches to hold a large number of samples. The niches may be all one size to hold samples appropriate for a single size sample carrier such as EM grids. Alternatively, the wafer facsimile may be formed with niches of several different sizes, with the size of a given niche appropriate for variations in the EM lamella grid being used. Some of the samples will be removed from their niches for testing, while other samples may be tested in situ on the wafer facsimile. For example, a sample may be an entire semiconductor chip removed from the wafer. Such a chip can be subject to electronic testing on the wafer facsimile. In one embodiment, the wafer facsimile acts as an electronic testing platform.

In certain embodiments, the TEM grids may clamped or otherwise "retained" in their receptacles by various means including whole or partial "lids" or clips to hold them in their receptacles.

In one embodiment, the niches are indexed such that each lamella is identifiable to the wafer and section thereof being tested. In certain embodiments the lamella location will be stored in a "wafer map" or other type of database. For example, on the wafer map, each niche may correspond to a grid number, such that each lamella sample from each tested wafer corresponds to a particular niche identified by that number (e.g., Sample×from Wafer×placed in Grid Number×20).

In an alternative embodiment, indexing using barcodes may be utilized to optically keep track of the samples being placed on the wafer facsimile. The tag such as a barcode could be placed on an available surface of the wafer facsimile (SCOW) for easy access by a scanning device. In certain FABs RFIDs are utilized on the FOUP. Thus certain embodiments provide for RFID tags on the SCOWs. Each wafer facsimile (SCOW), having a unique, identifiable tag, could then be associated with particular samples from a particular wafer (e.g., barcode or RFID matched with samples from Wafer #x). In this way, the level of automation between sample preparation, transport and testing is improved to increase efficiency of the manufacturing process.

In yet another embodiment, the lamella production tool may transmit data corresponding to the particular lamella being prepared to the factory automation computer services or to other FAB equipment, such as through a network. The imaging tool, for example, would then receive the data over the network so as to be able to identify the particular lamella being imaged at any given time.

In one embodiment, the wafer facsimile (SCOW) is loaded into an EM sample preparation tool adjacent to a wafer from which test samples are taken. The EM preparation tool prepares the EM lamella from the wafer, detaches them, and then transfers and attaches them to EM grids placed in the niches in the wafer facsimile. Once the desired lamella are positioned in sample niches on the wafer facsimile (SCOW), factory AMHS equipment is then able move the wafer facsimiles (SCOWS) into FOUPs and move them around the FAB. In certain embodiments, the sample containing FOUPs will not carry wafers from which samples were taken. In other embodiments, the FOUP stores a plurality of wafers and further contains one or more wafer facsimiles (SCOWs) that include samples from each of the wafers in the FOUP. The FOUP could then be delivered from Tool A to Tool B using ARMS equipment, such as through the use of overhead track systems of the ARMS. For example, in a standard FOUP designed to hold 25 wafers, the FOUP could be carrying 24 of the wafers to be tested, together with one wafer facsimile that is carrying all of the EM lamella from those 24 wafers.

Figure 4:
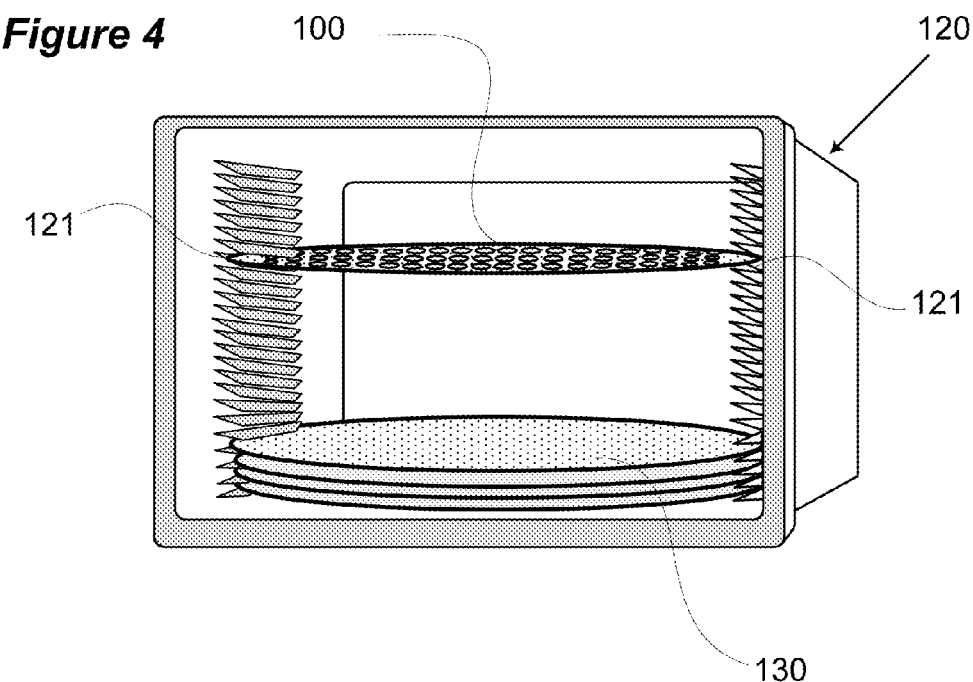
FIG. 4 depicts an embodiment of a wafer facsimile in a simplified drawing of a FOUP together with semiconductor wafers corresponding to the samples on the wafer facsimile. Not shown is a typical "flange" on top that is the means by which factory automation "grabs" the FOUP.

FIG. 4 demonstrates an embodiment of a wafer facsimile 100 in a simplified drawing of a FOUP 120 together with a plurality of semiconductor wafers 130 corresponding to the samples on the wafer facsimile. Not shown is a typical "flange" on top that is the means by which factory automation "grabs" the FOUP. As depicted, FOUP 120 is dimensioned to hold a class of semiconductor wafers 130 having a particular diameter with at least two opposite edges of the wafer resting on fins 121 projecting from at least two opposing sides of the FOUP. In this embodiment, the wafer facsimile 100 will have an outer dimensioned adapted to fit within and rest on the fins 121 of the FOUP dimensioned for the class of semiconductor wafers being moved through the FAB. A similar arrangement would apply if the wafers are data storage wafers.

The wafer facsimiles (SCOWs) may each be carried individually in a designated FOUP to be used only for transporting, storing and testing wafer facsimiles (SCOWs), so as to avoid potential wafer contamination. In many cases, the wafer that the lamella is removed from would be "scrapped." Most FOUP "front ends" have the ability to have two FOUPS loaded at once, so the TEM preparation tool is readily adaptable to have the EM grids loaded onto a FOUP used only for EM grids.

Figure 5:
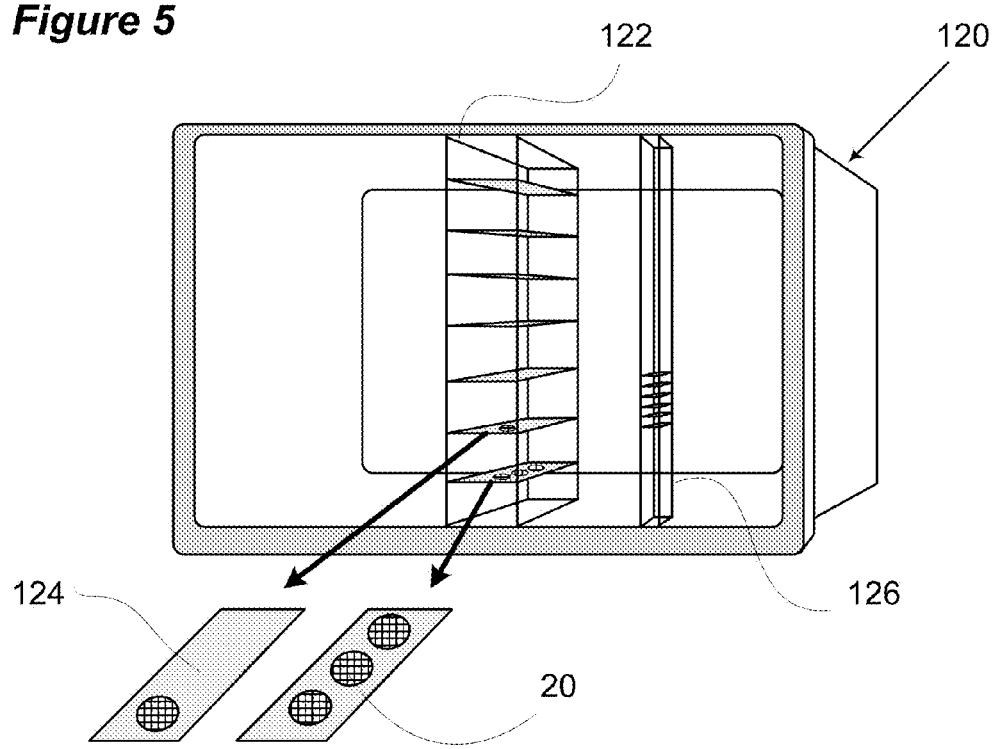
FIG. 5 depicts an embodiment in which a FOUP is modified to include a sample tower that can hold sample trays on which TEM grids and/or lamella can be deposited. Thus, the FOUP has locations to directly receive the TEM lamella in the absence of a wafer facsimile. Again not shown is a typical "flange" on top that is the means by which factory automation "grabs" the FOUP.

FIG. 5 depicts an alternative embodiment in which the FOUP is modified to have an insert such as depicted tower 122 or tower 126 that function as depositories for TEM grids, lamella supports and/or other holders for samples to be tested. The FOUP may contain one tower or a plurality of towers across the face of the FOUP. The tower may be small relative to the overall FOUP dimensions. Thus the tower may be, for example, 4 mm wide, 4 mm deep, and as tall as is necessary for the desired number of slits as generally depicted as tower 126 (note that this is not depicted to scale as such a tower would be much narrower in a FOUP for 300 mm wafers). The front of the towers are positioned at the entry front of the FOUP. Alternatively a larger tower such as depicted tower 122 may hold one or more "trays" 124 that hold one or more sample to be tested. The towers may be permanently installed or may be a removable insert in a standard FOUP with retention by brackets or the like. A robot may be employed to insert TEM grids or lamella or other samples into the appropriate slots in the "modified" FOUP.

Example 2

Figure 2A:
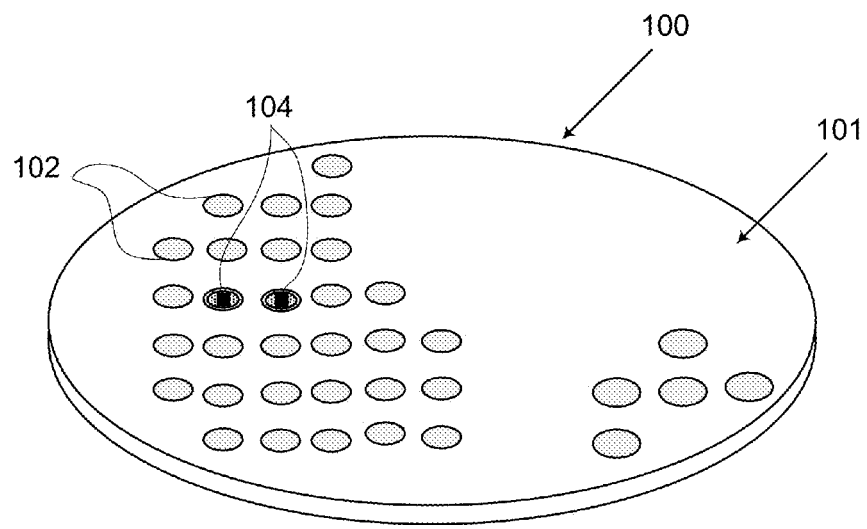
FIG. 2A represents an oblique top down view of a wafer facsimile according to one embodiment of the present invention.
Figure 2B:
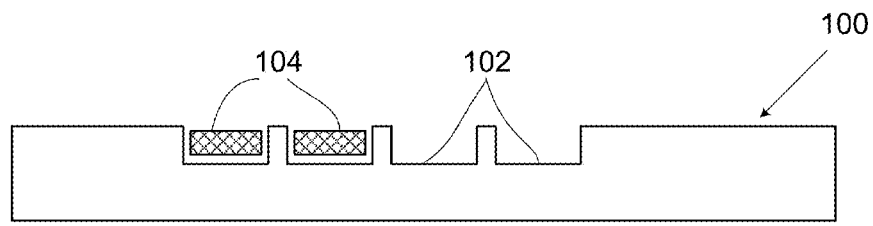
FIG. 2B is a partial side view of the wafer facsimile illustrated in FIG. 2A.

In another embodiment, as illustrated in FIGS. 2A-B, a wafer facsimile (SCOW) 100 includes a plurality of sample niches in the form of EM grid receptacles 102. FIG. 2A provides an oblique top down view while FIG. 2B presents a partial side view showing that the niches are formed as depressions in the surface of the wafer facsimile. While FIG. 2A illustrates a wafer facsimile (SCOW) 100 having EM grid receptacles 102 covering only a portion of the upper surface 101 of the wafer facsimile 100, it is envisioned that EM grid receptacles 102 could extend across much of the surface of the wafer facsimile (SCOW) 100. Each EM grid receptacle 102 carries an EM grid 104 which carries an EM lamella. Specifically, the wafer facsimile 100 is first loaded into an EM sample preparation tool adjacent to the wafer that is to be tested. The EM grids 104 are already positioned in the EM grid receptacles 102. The EM sample preparation tool forms the EM lamella samples from the wafers and then attaches them to the EM grids 104 using the methods disclosed herein. The wafer facsimile 100 carrying the plurality of EM grids 104 is then transferred to the EM analysis tool using a FOUP (not shown). In one embodiment an EM analysis tool is designed to include a FOUP handler that receives the FOUP and fully or partially extracts the wafer facsimile for removal of selected EM samples from their sample niches. The EM FOUP handler includes a mechanism to lift the EM grids 104 from the wafer facsimile 100 and bring them into the EM for imaging analysis.

In certain embodiments, a micromanipulator and a hollow microprobe probe use vacuum pressure to adhere the microprobe tip to the sample. By applying a small vacuum pressure to the lamella through the microprobe tip, the lamella can be held more securely and its placement controlled more accurately than by using electrostatic force alone. One such mechanism is described in U.S. Pat. No. 8,357,913, incorporated herein by reference.

Figure 3:
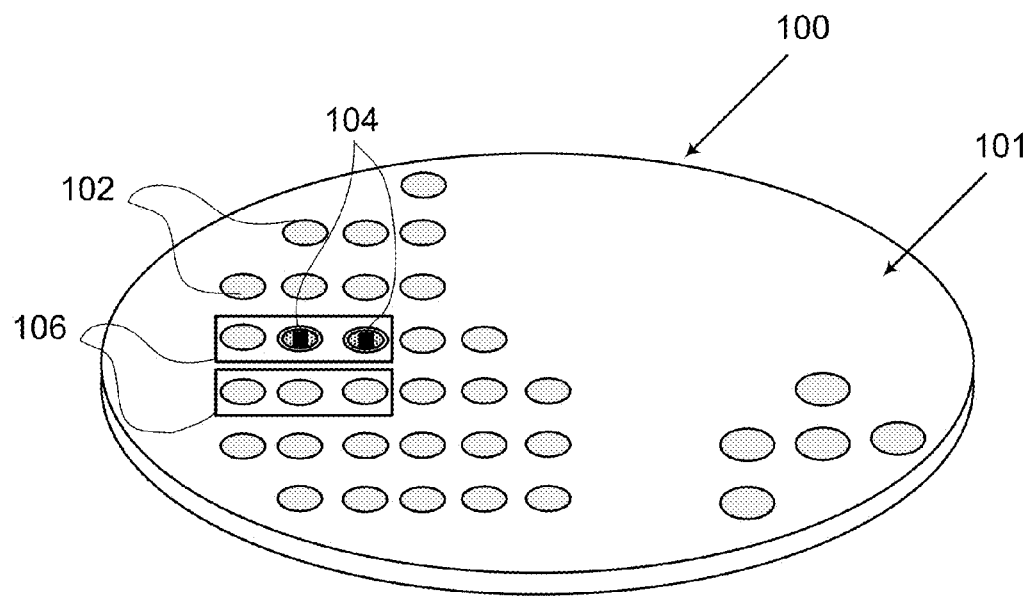
FIG. 3 is a top perspective view of the wafer facsimile illustrated in FIG. 2A, having sub-carriers.

In a variation on EM sample handling, as illustrated in FIG. 3, the wafer facsimile (SCOW) 100 includes at least one sub-carrier 106. The sub-carrier 106 is positioned on or in the upper surface 101 of the wafer facsimile 100 and is designed to carry a plurality of TEM grid receptacles 102. In one embodiment, the sub-carrier 106 includes two, three or more EM grid receptacles 102, so as to be able to carry a plurality of EM grids 104. The sub-carrier 106 can then be detached or otherwise separated from the wafer facsimile 100 by the EM analysis tool and the entire sub-carrier 106 may be placed inside the vacuum chamber of the EM analysis tool for serial imaging. This method increases the efficiency of the imaging system, as it allows for more than one EM sample placed in the vacuum of the EM tool at once. Thus in certain embodiments, the subcarrier is used in conjunction with an EM "autoloader." The autoloader is adapted to work in conjunction with a "cassette" that holds a number of EM grids. This cassette is adapted to be loaded/unloaded from an EM that has a special option to use this feature.

In one embodiment, the sub-carrier 106 is formed of the same material as the wafer facsimile 100 and is preferably sized such that it fits within the vacuum chamber of the EM analysis tool. The number of dimensions of the sub-carrier and thus the number of grids that can be held on the carrier are limited only by the internal dimensions of the sample chamber of the EM device.

The wafer facsimiles in this Example are preferably designed with the same size, shape and material as those disclosed in Example 1. In certain embodiments, the actual thickness of the facsimile wafer may, if necessary, be a bit thicker than standard wafers and yet still be compatible with wafer and FOUP handling equipment.

Example 3

The primary factory automation of FOUPs can be considered to be split into three parts. First, the FOUPs are moved around from location to location via the AMHS. This is typically done by grabbing onto a "flange" on the top of the FOUP. The contents of the FOUP are irrelevant to this process as long as the exterior configuration and weight of the FOUP is compatible with the AMHS. A second aspect of FOUP handling is opening the front "door" of the FOUP and conversely closing it. Again it doesn't matter what's inside the FOUP for this to happen. As far as overhead track and FOUP delivery is concerned these are the only two important aspects of the FOUP handling system. The final part is usually performed by the individual processing or metrology equipment that vendors apply. After FOUPs are opened up, a robot can grab a wafer out of the FOUP.

In another embodiment, EM lamella are loaded into a modified FOUP in a manner in which no wafer or wafer facsimile is needed. In this embodiment, once the EM lamella are prepared by the lamella preparation tool, they are directly loaded into small slots in a modified FOUP that is designed to receive lamella directly, instead of having to use wafer facsimiles. The modified FOUP is preferably compatible with FOUP handling equipment of the AMHS. In one such embodiment, a modified FOUP is provided with a cassette having a plurality of slots that each hold an EM grid. For one non-limiting example, the cassette would be about one (1) inch tall (2.54 cm) and about 4 mm wide and configured to hold a plurality of EM grids. The outside of the modified FOUP would still be compatible with other AMHS equipment, such that it is able to be moved around the FAB using existing AMHS equipment, but the inside of the modified FOUP is configured to receive cassettes, such as those set forth above, as opposed to semiconductor wafers.

Figure 6:
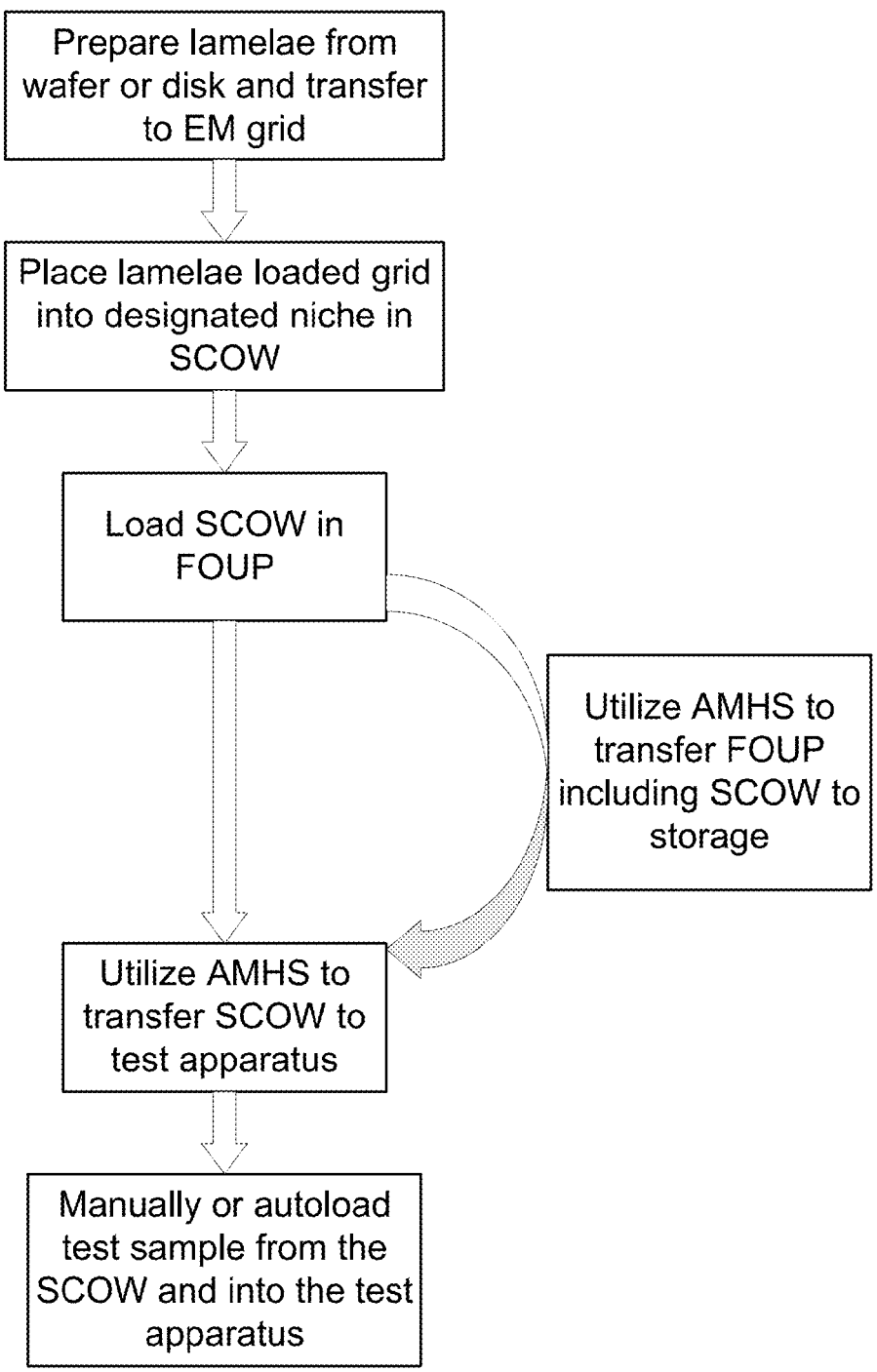
FIG. 6 depicts a process flowchart according to one embodiment.

FIG. 6 depicts one embodiment of a flow of a lamella or other test sample through a FAB or data storage facility via a sample carrier that is dimensioned to fit in a FOUP and be transported via the AMHS system of the facility. As depicted the lamella or other test sample are prepared from a semiconductor wafer or a data storage disk and transferred to an EM grid or other test substrate. The test sample loaded EM grid or substrate is placed in a designated niche in a SCOW. The SCOW is loaded into a FOUP. The SCOW may then be conveyed via the AMHS to storage or may be conveyed directly to test apparatus including those adapted to perform any one or combination of TEM, SEM, STEM, Dual Beam, EDS, EDX, and EELS testing as well as any electronic or other testing that might be desired.

Example 4

In another embodiment, EM lamella or lamella loaded on EM grids are loaded directly into appropriately dimensioned slots in a carrier having an outer dimension that corresponds to a FOUP and is compatible with FOUP handling equipment, but which has provisions for directly receiving EM lamella or EM grids. In other embodiments, the EM lamella are loaded in an intermediary carrier that is loaded into an appropriately modified FOUP. In either event, a FOUP is used to move around EM lamella through the FAB or data storage facility. In one case, the FOUP moves wafers with lamella attached, in another embodiments the FOUP moves wafer-like objects, herein termed SCOWS, that function as carriers and data mapped storage devices for EM grids. In these embodiments, an EM imaging tool or other sample test apparatus receives a FOUP containing samples in one of the disclosed forms.

In certain embodiments the test instrument such as an EM device is adapted to include a mechanical mechanism that receives the FOUPs and functions as an EM-instrument-plus-FOUP-handler.

Figure 7:
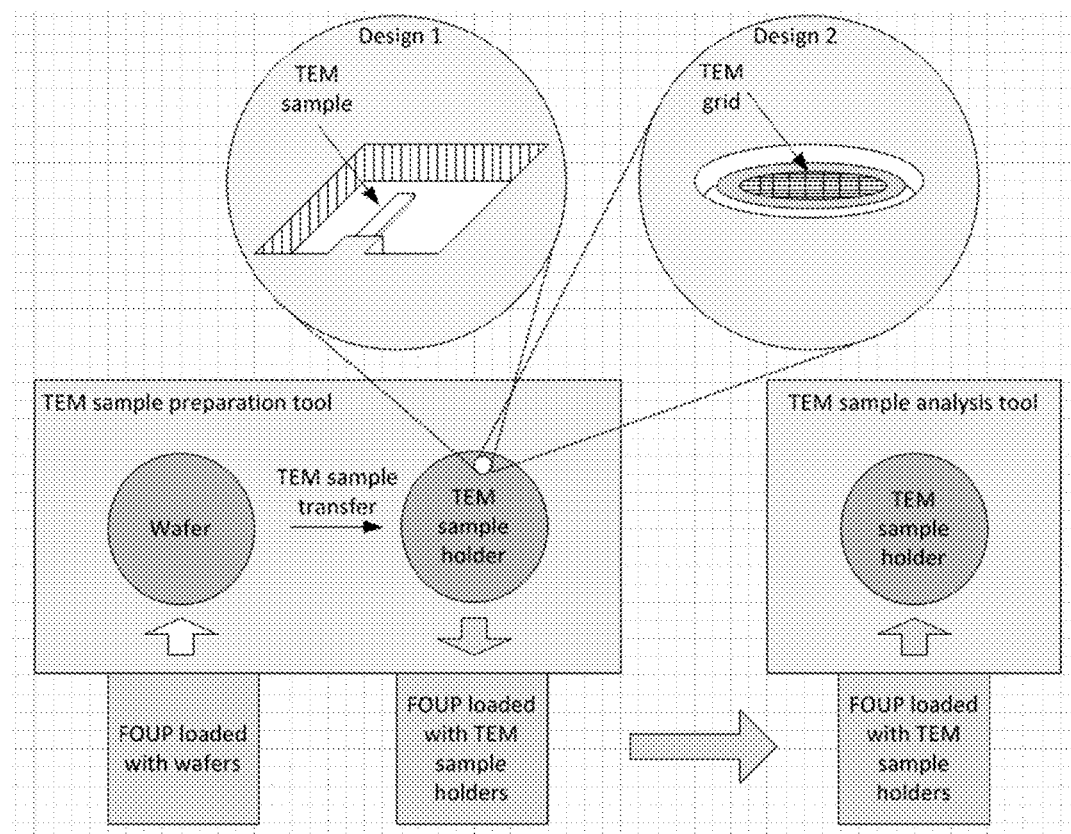
FIG. 7 depicts a process including the utilization of FOUPs through the sample collection and analysis process.

As depicted in FIG. 7, in one embodiment a process is provided that includes movement of a FOUP loaded with wafers to an EM sample preparation tool. A wafer is removed from the FOUP and a sample is prepared. For example, a site-specific region of the wafer is milled such as with a focused ion beam (FIB) to electron transparency. The thin lamella is removed from its "trench" with a micromanipulator. In certain embodiments, the sample may attach to the micromanipulator tip via electrostatic forces and be removed from its trench. These samples, termed ex situ lift-out (EXLO) samples, are transferred to a wafer shaped EM sample holder using automated techniques. The sample may be directed mounted to a sample holding platform or post in the wafer shaped EM sample holder (Design 1). Alternatively, the sample may be transferred to carbon-coated EM grids, formvar-coated grids, holey carbon grids, or directly to the surface of small mesh EM grids using automated routines (Design 2). On a 300 mm EM sample holder, there will be space for hundreds of cells or niches for EM samples. In certain embodiments, the EM preparation tool is able to prepare EM samples, detach them from the wafer, and transfer and attach them to an EM sample holder wafer (wafer facsimile). The preparation tool may be adapted to load a regular wafer and EM sample holder wafer side-by-side. After a sufficient number of samples are loaded onto the sample holder wafer, the EM sample holder wafer shall be unloaded to a FOUP and transferred to an EM analysis tool. In certain embodiments, the samples are loaded into the EM chamber, brought into the electron beam and analyzed. After the analysis, the EM sample holder wafer can either be cleaned for re-use, or stored for later further analysis or re-evaluation of the collected samples. In certain embodiments, a "library" of samples is stored respective to various lots of wafers.

In an alternative designed, the wafer-like sample holder is designed with through-holes for TEM analysis. TEM samples are attached to the holder and located over the hole. TEM sample analysis tool has a mechanism to bring holes with TEM samples attached under the beam.

Example 5

In one embodiment, workflow through the FAB includes the FOUP being received by an EFEM attached to the TEM. The FOUP door is opened, and the SCOW is removed. A small robot picks out a TEM grid of interest and loads it into a TEM holder. The TEM holder is loaded into the TEM. Typically the process will be automated. In another embodiment, a small robot picks out a TEM grid of interest and loads it into an "autoloader" cassette (such as those available from FEI Co.). The autoloader cassette is loaded into the TEM and existing infrastructure allows the TEM grid of interest to be placed onto a TEM grid holder.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

We claim:

1. A wafer or disk facsimile for use in storing and transporting test samples taken from a semiconductor wafer or data storage wafer, comprising:
    a body dimensioned to correspond to at least a diameter of the semiconductor wafer or data storage wafer from which the test samples are taken; and
    a plurality of niches formed in a surface of the body and configured to receive one or more of the test samples taken from the semiconductor wafer or data storage wafer.

2. The wafer or disk facsimile of claim 1, wherein the test samples are electron microscope (EM) lamella.

3. The wafer or disk facsimile of claim 2, wherein the test samples are transmission electron microscope (TEM) and/or scanning/transmission electron microscope (STEM) lamella.

4. The wafer or disk facsimile of claim 1, wherein the body is formed of a rigid material configured to be received and transported by a front opening unified pod (FOUP).

5. The wafer or disk facsimile of claim 4, wherein the rigid material is a ceramic, plastic, metal or silicon material.

6. The wafer or disk facsimile of claim 1, wherein each of the plurality of niches are configured to directly receive a test sample.

7. The wafer or disk facsimile of claim 1, wherein the plurality of niches are EM grid receptacles configured to receive EM grids.

8. The wafer or disk facsimile of claim 1, wherein the plurality of niches include EM grid retainers.

9. The wafer or disk facsimile of claim 7, further comprising at least one sub-carrier positioned on or in a surface of the wafer facsimile, the at least one sub-carrier configured to carry a plurality of EM grids such that the sub-carrier may be loaded directly into a vacuum chamber of an electron microscope (EM).

10. The wafer facsimile of claim 9, wherein the sub-carrier is configured to carry transmission electron microscope (TEM) grids.

11. The wafer facsimile of claim 1, wherein the plurality of niches is indexed such that each test sample received therein is identifiable to a semiconductor wafer or data storage wafer from which the test sample is taken.

12. The wafer facsimile of claim 11, wherein the plurality of niches are indexed using a barcode or an RFID tag.

13. A wafer facsimile for use in storing and transporting test samples taken from a data storage wafer or a solar cell wafer, comprising:
    a body dimensioned to correspond to an outer diameter of the data storage wafer or solar cell wafer being tested; and
    a plurality of niches formed in a surface of the body and configured to receive one or more test samples.

14. The wafer facsimile of 13, wherein the plurality of niches is indexed such that each test sample received therein is identifiable to a semiconductor wafer or data storage wafer from which the test sample is taken.

* * * * *